(12) United States Patent
Moeller et al.

(10) Patent No.: US 7,193,116 B2
(45) Date of Patent: Mar. 20, 2007

(54) METHOD FOR PRODUCING ALDEHYDES BY MEANS OF HYDROFORMYLATION OF OLEFINICALLY UNSATURATED COMPOUNDS, SAID HYDROFORMYLATION BEING CATALYZED BY UNMODIFIED METAL COMPLEXES IN THE PRESENCE OF CYCLIC CARBONIC ACID ESTERS

(75) Inventors: Oliver Moeller, Recklinghausen (DE); Klaus-Diether Wiese, Haltern am See (DE); Dieter Hess, Marl (DE); Cornelia Borgmann, Frankfurt (DE); Alfred Kaizik, Marl (DE); Dirk Fridag, Haltern am See (DE)

(73) Assignee: OXENO Olefinchemie GmbH, Marl (DE)

( * ) Notice: Subject to any disclaimer, the term of this patent is extended or adjusted under 35 U.S.C. 154(b) by 0 days.

(21) Appl. No.: 10/519,557

(22) PCT Filed: Aug. 7, 2003

(86) PCT No.: PCT/EP03/08737

§ 371 (c)(1),
(2), (4) Date: Dec. 28, 2004

(87) PCT Pub. No.: WO2004/024661

PCT Pub. Date: Mar. 25, 2004

(65) Prior Publication Data

US 2005/0209489 A1 Sep. 22, 2005

(30) Foreign Application Priority Data

Aug. 31, 2002 (DE) ............................. 102 40 253
Jun. 18, 2003 (DE) ............................. 103 27 439

(51) Int. Cl.
C07C 45/50 (2006.01)
(52) U.S. Cl. .................................... 568/451; 568/454
(58) Field of Classification Search .................... None
See application file for complete search history.

(56) References Cited

U.S. PATENT DOCUMENTS

| | | | |
|---|---|---|---|
| 3,992,453 A | 11/1976 | Massie ................... 860/604 |
| 4,490,559 A | 12/1984 | Wegman et al. ........... 568/484 |
| 5,012,008 A * | 4/1991 | Drago et al. ............. 568/454 |
| 5,093,534 A | 3/1992 | Ludwig et al. |
| 6,015,928 A | 1/2000 | Gubisch et al. |
| 6,184,424 B1 | 2/2001 | Bueschken et al. |
| 6,239,318 B1 | 5/2001 | Schuler et al. |
| 6,331,657 B1 | 12/2001 | Kaizik et al. |
| 6,403,836 B2 | 6/2002 | Kaizik et al. |
| 6,403,837 B1 | 6/2002 | Hess et al. |
| 6,407,295 B1 | 6/2002 | Kaizik et al. |
| 6,482,992 B2 | 11/2002 | Scholz et al. |
| 6,492,564 B1 | 12/2002 | Wiese et al. |
| 6,500,991 B2 | 12/2002 | Wiese et al. |
| 6,555,716 B2 | 4/2003 | Protzmann et al. |
| 6,570,033 B2 | 5/2003 | Rottger et al. |
| 6,627,782 B2 | 9/2003 | Kaizik et al. |
| 6,680,414 B2 | 1/2004 | Knoop et al. |
| 6,720,457 B2 | 4/2004 | Drees et al. |
| 6,818,770 B2 | 11/2004 | Selent et al. |
| 6,924,389 B2 | 8/2005 | Jackstell et al. |
| 6,956,133 B2 | 10/2005 | Jackstell et al. |
| 6,960,699 B2 | 11/2005 | Totsch et al. |
| 7,009,068 B2 | 3/2006 | Schmutzler et al. |
| 7,109,346 B2 | 9/2006 | Beller et al. |
| 2003/0144559 A1 | 7/2003 | Hess et al. |
| 2003/0195368 A1 | 10/2003 | Rottger et al. |
| 2004/0236133 A1 | 11/2004 | Selent et al. |
| 2004/0238787 A1 | 12/2004 | Wiese et al. |
| 2004/0242947 A1 | 12/2004 | Beller et al. |
| 2005/0209489 A1 | 12/2004 | Moeller et al. |
| 2005/0043279 A1 | 2/2005 | Selent et al. |
| 2005/0171371 A1 | 8/2005 | Borner et al. |
| 2005/0182277 A1 | 8/2005 | Totsch et al. |
| 2005/0208455 A1 | 9/2005 | Boerner et al. |
| 2005/0209455 A1 | 9/2005 | Boerner et al. |
| 2005/0234270 A1 | 10/2005 | Kaizik et al. |
| 2005/0256281 A1 | 11/2005 | Grund et al. |
| 2006/0036121 A1 | 2/2006 | Kaizik et al. |
| 2006/0089469 A1 | 4/2006 | Komarov et al. |
| 2006/0128998 A1 | 6/2006 | Lueken et al. |
| 2006/0129004 A1 | 6/2006 | Lueken et al. |
| 2006/0161017 A1 | 7/2006 | Grass et al. |
| 2006/0183936 A1 | 8/2006 | Grass et al. |

FOREIGN PATENT DOCUMENTS

| DE | 35 11 428 | 10/1986 |
|---|---|---|
| WO | 87/07261 | 12/1987 |

OTHER PUBLICATIONS

U.S. Appl. No. 10/525,376, filed Feb. 23, 2005, Moeller, et al.
U.S. Appl. No. 10/519,557, filed Dec. 28, 2004, Moeller et al.,
U.S. Appl. No. 11/494,741, filed Jul. 28, 2006, Kaizik et al.
U.S. Appl. No. 10/562,454, filed Aug. 18, 2006, Krissmann et al.
U.S. Appl. No. 10/576,302, filed Apr. 19, 2006, Kaizik et al.
U.S. Appl. No. 10/588,762, filed Aug. 8, 2006, Wiese, et al.
U.S. Appl. No. 10/593,330, filed Sep. 19, 2006, Borgmann et al.
U.S. Appl. No. 10/584,492, filed Jun. 22, 2006, Ortmann et al.
U.S. Appl. No. 10/584,148, filed Jun. 22, 2006, Ortmann et al.
U.S. Appl. No. 09/708,646, filed Nov. 9, 2000, Hess et al.
U.S. Appl. No. 10/505,879, filed Sep. 3, 2004, Borgmann.

* cited by examiner

*Primary Examiner*—Sikarl A. Witherspoon
(74) *Attorney, Agent, or Firm*—Oblon, Spivak, McClelland, Maier & Neustadt, P.C.

(57) ABSTRACT

The present invention relates to a process for preparing aldehydes by hydroformylation catalyzed by metals of groups 8 to 10 of the Periodic Table of the Elements in the presence of cyclic carbonic esters.

21 Claims, 2 Drawing Sheets

METHOD FOR PRODUCING ALDEHYDES BY MEANS OF HYDROFORMYLATION OF OLEFINICALLY UNSATURATED COMPOUNDS, SAID HYDROFORMYLATION BEING CATALYZED BY UNMODIFIED METAL COMPLEXES IN THE PRESENCE OF CYCLIC CARBONIC ACID ESTERS

CROSS REFERENCES TO RELATED APPLICATIONS

This application is a national stage application of International Patent Application No. PCT/EP03/08737, filed on Aug. 7, 2003, and claims priority to German Patent Application No. 102 40 253.1, filed on Aug. 31, 2002, and German Patent Application No. 103 27 435.9, filed on Jun. 18, 2003, all of which are incorporated herein by reference.

BACKGROUND OF THE INVENTION

1. Field of the Invention

The present invention relates to a process for preparing aldehydes by hydroformylation of olefinically unsaturated compounds, in particular olefins, catalyzed by an unmodified metal catalyst derived from a metal of groups 8 to 10 of the Periodic Table of the Elements, which process is carried out in the presence of cyclic carbonic esters as solvents.

2. Discussion of the Background

The reactions of olefin compounds, carbon monoxide and hydrogen in the presence of a catalyst to form the aldehydes having one more carbon atom are known as hydroformylation (oxo process). Catalysts used in these reactions are frequently compounds of the transition metals of groups 8 to 10 of the Periodic Table of the Elements, in particular compounds of rhodium and of cobalt. In comparison with catalysis by cobalt compounds, hydroformylation using rhodium compounds generally offers the advantage of higher chemo-selectivity and regioselectivity and is therefore usually more economically attractive.

The rhodium-catalyzed hydroformylation is usually carried out using complexes comprising rhodium and compounds of group 15 of the Periodic Table of the Elements, preferably trivalent phosphorus compounds, as ligands. For example, compounds from the classes of phosphines, phosphites and phosphonites are frequently used as ligands. An overview of the hydroformylation of olefins may be found in B. CORNILS, W. A. HERRMANN, "Applied Homogeneous Catalysis with Organometallic Compounds", Vol. 1&2, VCH, Weinheim, N.Y., 1996.

Terminal olefins can easily be reacted in the presence of phosphine-modified rhodium catalysts. On the other hand, internal olefins and especially internal highly branched olefins require strongly activating ligands such as phosphite ligands. In addition, "naked" or unmodified rhodium has also been found to be well suited in the case of olefins which are difficult to hydroformylate. These catalysts comprise one or more metal species which are formed under hydroformylation conditions from a metal salt in the absence of modifying ligands. For the purposes of the present patent application, modifying ligands are compounds which contain one or more donor atoms of group 15 of the Periodic Table of the Elements. However, modifying ligands do not include alkoxy, carbonyl, hydrido, alkyl, aryl, allyl, acyl or alkene ligands, nor the counterions of the metal salts used for catalyst formation, e.g. halides such as fluoride, chloride, bromide or iodide, acetylacetonate, carboxylates such as acetate, 2-ethylhexanoate, hexanoate, octanoate or nonanoate.

Modifying ligands for the purposes of the present patent application are ligands which contain donor atoms from group 15 of the Periodic Table of the Elements, for example nitrogen, phosphorus, arsenic or antimony, in particular phosphorus. The ligands can be monodentate or polydentate, and in the case of chiral ligands, either the racemate or one enantiomer or diastereomer can be used. Particularly important examples of phosphorus ligands are phosphines, phosphinines, phosphinanes, phosphine oxides, phosphites, phosphonites and phosphinites.

Examples of phosphines are triphenylphosphine, tris(p-tolyl)phosphine, tris(m-tolyl)phosphine, tris(o-tolyl)phosphine, tris(p-methoxyphenyl)phosphine, tris(p-fluorophenyl)phosphine, tris(p-chlorophenyl)phosphine, tris(p-dimethylaminophenyl)phosphine, ethyldiphenylphosphine, propyldiphenylphosphine, t-butyldiphenylphosphine, n-butyldiphenylphosphine, n-hexyldiphenylphosphine, c-hexyldiphenylphosphine, dicyclohexylphenylphosphine, tricyclohexylphosphine, tricyclopentylphosphine, triethylphosphine, tri(1-naphthyl)phosphine, tri-2-furylphosphine, tribenzylphosphine, benzyldiphenylphosphine, tri-n-butylphosphine, tri-i-butylphosphine, tri-t-butylphosphine, bis(2-methoxyphenyl)phenylphosphine, neomenthyldiphenylphosphine, the alkali metal, alkaline earth metal, ammonium or other salts of sulfonated triphenylphosphines such as tris(m-sulfonylphenyl)phosphine, (m-sulfonylphenyl)diphenylphosphine; 1,2-bis(dicyclohexylphosphino)ethane, bis(dicyclohexylphosphino)methane, 1,2-bis(diethylphosphino)ethane, 1,2-bis(2,5-diethylphospholano)benzene [Et-DUPHOS], 1,2-bis(2,5-diethylphospholano)ethane [Et-BPE], 1,2-bis(dimethylphosphino)ethane, bis(dimethylphosphino)methane, 1,2-bis(2,5-dimethylphospholano)benzene [Me-DUPHOS], 1,2-bis(2,5-dimethylphospholano)ethane [Me-BPE], 1,2-bis(diphenylphosphino)benzene, 2,3-bis(diphenylphosphino)bicyclo[2.2.1]hept-5-ene [NORPHOS], 2,2'-bis(diphenylphosphino)-1,1'-binaphthyl [BINAP], 2,2'-bis(diphenylphosphino)-1,1'-biphenyl [BISBI], 2,3-bis(diphenylphosphino)butane, 1,4-bis(diphenylphosphino)butane, 1,2-bis(diphenylphosphino)ethane, bis(2-diphenylphosphinoethyl)phenylphosphine, 1,1'-bis(diphenylphosphino)ferrocene, bis(diphenylphosphino)methane, 1,2-bis(diphenylphosphino)propane, 2,2'-bis-(di-p-tolylphosphino)-1,1'-binaphthyl, O-isopropylidene-2,3-dihydroxy-1,4-bis(diphenylphosphino)butane [DIOP], 2-(diphenylphosphino)-2'-methoxy-1,1'-binaphthyl, 1-(2-diphenylphosphino-1-naphthyl)-isoquinoline, 1,1,1-tris(diphenylphosphino)ethane, and/or tris(hydroxypropyl)phosphine.

Examples of phosphinines include 2,6-dimethyl-4-phenyl-phosphinine, 2,6-bis(2,4-dimethylphenyl)-4-phenylphosphinine and also further ligands described in WO 00/55164. Examples of phosphinanes include 2,6-bis(2,4-dimethylphenyl)-1-octyl-4-phenylphosphinane, 1-octyl-2,4,6-triphenylphosphinane and further ligands described in WO 02/00669.

Examples of phosphites are trimethyl phosphite, triethyl phosphite, tri-n-propyl phosphite, tri-i-propyl phosphite, tri-n-butyl phosphite, tri-i-butyl phosphite, tri-t-butyl phosphite, tris(2-ethylhexyl)phosphite, triphenyl phosphite, tris(2,4-di-t-butylphenyl) phosphite, tris(2-t-butyl-4-methoxyphenyl) phosphite, tris(2-t-butyl-4-methylphenyl) phosphite, tris(p-cresyl) phosphite. Further examples are sterically hindered phosphite ligands as are described, inter alia, in EP 155 508, U.S. Pat. No. 4,668,651, U.S. Pat. No. 4,748,261, U.S. Pat. No. 4,769,498, U.S. Pat. No. 4,774,361, U.S. Pat. No. 4,835,299, U.S. Pat. No. 4,885,401, U.S. Pat. No. 5,059,710, U.S. Pat. No. 5,113,022, U.S. Pat. No. 5,179,055, U.S. Pat. No. 5,260,491, U.S. Pat. No. 5,264,616, U.S. Pat. No. 5,288,918, U.S. Pat. No. 5,360,938, EP 472 071, EP 518 241 and WO 97/20795. Among the sterically hindered phosphites, mention may be made of the triphenyl phosphites which are substituted by 1 or 2 isopropyl and/or tert-butyl substituents, preferably in the ortho position relative to the phosphite ester group. Further bisphosphite ligands are mentioned, inter alia, in EP 1 099 677, EP 1 099 678, WO 02/00670, JP 10279587, EP 472017, WO 01/21627, WO 97/40001, WO 97/40002, U.S. Pat. No. 4,769,498, EP 213639 and EP 214622.

Examples of phosphonites are methyldiethoxyphosphine, phenyldimethoxyphosphine, phenyldiphenoxyphosphine, 6-phenoxy-6H-dibenz[c,e][1,2]oxaphosphorin and their derivatives in which all or some of the hydrogen atoms are replaced by alkyl or aryl radicals or halogen atoms and ligands as described in WO 98/43935, JP 09-268152 and DE 198 10 794 and in the German patent applications DE 199 54 721 and DE 199 54 510.

Customary phosphinite ligands are described, inter alia, in U.S. Pat. No. 5,710,344, WO 95 06627, U.S. Pat. No. 5,360,938, JP 07082281. Examples are diphenyl(phenoxy) phosphine and its derivatives in which all or some of the hydrogen atoms are replaced by alkyl or aryl radicals or halogen atoms, diphenyl(methoxy)phosphine, diphenyl (ethoxy)phosphine, etc.

In industrial hydroformylation, the reaction product, unreacted starting material and catalyst are usually separated by distillation. The hydroformylation is therefore carried out in the presence of a high-boiling solvent so that the work-up by distillation gives a high-boiling catalyst-containing fraction which can be recirculated to the process. In many continuous industrial hydroformylation processes in which rhodium catalysts are used, the high-boiling mixtures formed as by-product in the hydroformylation are used as solvents, as described, for example, in DE 2 062 703, DE 2 715 685, DE 2 802 922, EP 017183.

In addition to the high boilers, it is possible to use inert organic liquids (DE 3 126 265) and reaction products (aldehydes, alcohols), aliphatic and aromatic hydrocarbons, esters, ethers and water (DE 4 419 898) as solvents. In GB 1 197 902, saturated hydrocarbons, aromatics, alcohols and n-paraffins are used for this purpose.

The addition of one or more polar organic substances in the hydroformylation process is disclosed, for example, in WO 01/68248, WO 01/68249, WO 01/68252. For the present purposes, polar substances are substances from the following classes of compounds: nitriles, cyclic acetals, alcohols, pyrrolidones, lactones, formamides, sulfoxides and water.

In the hydroformylation of relatively long-chain olefins ($C \geqq 6$), the separation of the catalyst from the reaction product and possibly unreacted starting materials by distillation requires high temperatures and low pressures. Sometimes considerable decomposition of the rhodium-containing catalyst takes place during this distillation, regardless of whether or not an additional ligand has been used. This results in the catalyst being lost to the process, which has a drastic adverse effect on the economics of the process.

The unmodified rhodium catalysts are found to be particularly unstable. The prevailing opinion among those skilled in the art is that the mononuclear complex $HRh(CO)_3$ is, in the absence of modifying ligands, the species which is active in the hydroformylation. The complex $HRh(CO)_3$ is stable only at temperatures below 20° C. and under high pressure (N. S. Imyanitov, *Rhodium Express*, (1995), 10/11, 3–64) and is in equilibrium with a binuclear species which itself is not active but serves as a reservoir of active catalyst (E. V. Slivinskii, Y. A. Rozovskii, G. A. Korneeva, V. I. Kurkin, *Kinetics and Catalysis* (1998), 39(6), 764–774) (A. R. El'man, V. I. Kurkin, E. V. Slivinskii, S. M. Loktev, *Neftekhimiya* (1990), 30(1), 46–52). Hydroformylation-inactive clusters of increasing molecular weight are formed from the binuclear rhodium carbonyl complex. Under the conditions of an intensive hydroformylation reaction, the formation of the low molecular weight clusters is reversible. It has been demonstrated that clusters up to $Rh_4(CO)_{12}$ can be regenerated. The stabilization of the active species under hydroformylation conditions has likewise been able to be demonstrated (Yu. B. Kagan, Y. A. Rozovskii, E. V. Slivinskii, G. A. Korneeva, V. I. Kurkin, S. M. Loktev, *Kinetika i Kataliz* (1987), 28(6), 1508–1511). In contrast, higher molecular weight clusters cannot be converted back into active species under hydroformylation conditions (Yu. B. Kagan, E. V. Slivinskii, V. I. Kurkin, G. A. Korneeva, R. A. Aranovich, N. N. Rzhevskaya, S. M. Loktev, *Neftekhimiya* (1985), 25(6), 791–797). The formation of clusters is generally the cause of and the first step in the formation of solid rhodium-containing precipitates. It occurs during work-up by distillation, but sometimes also under reaction conditions. Rhodium-containing precipitates deposit on walls of vessels and pipes. This leads to considerable economically disadvantageous catalyst losses and makes regular plant shutdowns and cleaning work necessary in industrial use. Rhodium precipitates have to be recovered by means of a complicated metallurgical route.

Because of the attractiveness of unmodified rhodium as hydroformylation catalyst on the one hand and its instability on the other hand, many processes for its circulation and/or recovery have been proposed.

A series of processes in which removal of the rhodium species from the reaction mixture is carried out by means of solid adsorbents are known. Thus, for example, DE 19 54 315 proposes weakly to strongly basic ion-exchange resins based on polystyrene as adsorbents. According to DE 20 45 416, regeneration of loaded ion-exchange resins can be carried out by treatment with mixtures of lower alcohols, aliphatic amines and water in the presence of oxygen. The rhodium present in the eluate is converted by evaporation and treatment with hydrochloric acid into rhodium chloride hydrate which can be reused as catalyst precursor. WO 02/20451 and U.S. Pat. No. 5,208,194 claim the recovery of rhodium from loaded ion exchangers by incineration of these and isolation of the rhodium as oxide from the ash obtained. In U.S. Pat. No. 4,388,279, salts of metals of groups 1 and 2 of the Periodic Table of the Elements, zeolitic molecular sieves and ion-exchange resins are proposed as adsorbents. WO 01/72679 claims a process for the adsorption of rhodium on activated carbon, polysilicic acids and aluminum oxides at elevated temperature in the presence of hydrogen. The patent EP 0 355 837 describes a process for the adsorption of rhodium on basic ion-exchange resins which are modified with ionically bound organophosphorus ligands. Regeneration of the resin is carried out by elution with a solution containing organophosphorus ligands. WO 97/03938 claims a process for the adsorption of active rhodium species and of impurities on acidic ion-exchange resins. Regeneration is carried out by elution of the impurities with a neutral solvent in a first step and subsequently by elution of the active rhodium species using an acidic solvent. The catalyst which has been recovered in this way is, if appropriate after rehydrogenation, reused in the hydroformylation.

A disadvantage of all the adsorptive processes for the recovery of rhodium is the not satisfactorily solved problem of reliberation of the active species. A person skilled in the art will know that the solvents or solvent mixtures proposed for this purpose are not inert in hydroformylation but lead to secondary reactions. For example, acidic solvents induce the highly exothermic and difficult-to-control aldolization of the aldehydes. Alcohols and amines undergo condensation reactions with aldehydes and thus reduce the product yield. It is therefore absolutely necessary to remove the abovementioned solvents or solvent mixtures before recirculation of the catalyst. This makes the recovery concept extremely technically complicated and expensive. In contrast, adsorption on ion exchangers with subsequent ashing and metallurgical rhodium recovery has attained some industrial importance. This process is technically simple but nevertheless capable of improvement: an expensive basic ion exchanger is used as a consumable material and ashing with subsequent metallurgical work-up of the metal oxides is associated with further extremely complicated process steps.

Also known are a series of processes in which rhodium is extracted from the output from the reactor by means of solutions of various complexing agents and is recirculated to the hydroformylation reactor after it has been liberated again. Thus, for example, rhodium-catalyzed hydroformylation in the presence of protonable nitrogen-containing ligands, extraction of the rhodium complex with aqueous acid, deprotonation and recirculation of the rhodium to the process is known from DE 196 03 201. In DE 4 230 871, the aqueous solution is recirculated directly to the reaction. In EP 0 538 732, extraction of the output from the reactor with aqueous phosphine solution under synthesis gas pressure is claimed. WO 97/03938 claims water-soluble polymers such as polyacrylic acids, maleic acid copolymers and phosphonomethylated polyvinylamines, polyethylenimines and polyacrylamides as complexing agents. EP 0 588 225 claims pyridines, quinolines, 2,2'-bipyridines, 1,10-phenanthrolines, 2,2'-biquinolines, 2,2',6',2''-terpyridines and porphyrins, possibly in sulfonated and/or carboxylated form, as complexing agents. However, the complexing agents necessary in aqueous extraction are often expensive and hard to obtain. In addition, these processes involving two additional steps (extraction and catalyst liberation) require an increased engineering outlay.

Furthermore, processes in which rhodium precipitates in the classical work-up of the output from the reactor by distillation are said to be prevented by addition of phosphorus(III)-containing ligands are also known (DE 33 38 340, U.S. Pat. No. 4,400,547). The regeneration or reliberation of the hydroformylation-active rhodium species is carried out by oxidation of the phosphorus(III) ligands. A disadvantage of this process is the continuous stabilizer consumption. The phosphorus(V) compounds formed have to be discharged continually to prevent accumulation in the reactor system. Part of the rhodium in active form is unavoidably discharged too. This process, too, is therefore capable of improvement both technically and economically.

WO 82/03856 claims the distillation of the output from the hydroformylation reactor in the presence of oxygen. In the presence of oxygen, part of the aldehydes formed in the hydroformylation is oxidized to the corresponding carboxylic acids which react with the rhodium species to form soluble rhodium carboxylates. The rhodium carboxylates can be recirculated to the process. A disadvantage of this process is a reduced yield of desired product.

The as yet unpublished patent application DE 102 40 253 describes hydroformylation in the presence of catalysts based on metals of groups 8 to 10 of the Periodic Table of the Elements and modified by phosphorus ligands, with cyclic carbonic esters being used as solvents. The use of unmodified metal complexes of metals of groups 8 to 10 of the Periodic Table is not described.

JP 10-226662 describes a process for the hydroformylation of olefinic compounds in which a rhodium catalyst is used together with a sodium salt of sulfonated triphenylphosphines as cocatalyst, i.e. a modified catalyst is used. The reaction is carried out in the presence of a polar component and a carboxylic acid. The polar component can be, for example, ethylene carbonate. The polar component can be recirculated to the hydroformylation reaction together with the acid and the catalyst. However, the process can be used only for the hydroformylation of terminal olefins, which are comparatively reactive. In the case of internal olefins and especially internal highly branched olefins, the activity of the catalyst is far below that required for industrial uses.

The processes known hitherto for circulation or recovery of rhodium from processes which utilize unmodified rhodium as hydroformylation catalyst are capable of improvement from both a technical and an economic point of view.

SUMMARY OF THE INVENTION

Accordingly, the prior art includes no technically and economically satisfactory process for the hydroformylation of olefins which are difficult to hydroformylate using unmodified rhodium as catalyst. It is therefore an object of the invention to provide a process which is considerably improved in this respect, in particular a process in which catalyst recovery can be carried out simply and which displays considerably reduced catalyst deactivation and is therefore able to prevent losses of catalyst to a large degree.

It has now surprisingly been found that in the hydroformylation of olefinically unsaturated compounds, selectivity and activity can be increased and the work-up of the reaction mixture can be made easier and the catalyst stability can be increased considerably when the hydroformylation catalyzed by unmodified rhodium is carried out in the presence of cyclic carbonic esters as solvents.

DETAILED DESCRIPTION OF THE INVENTION

Figure 1:
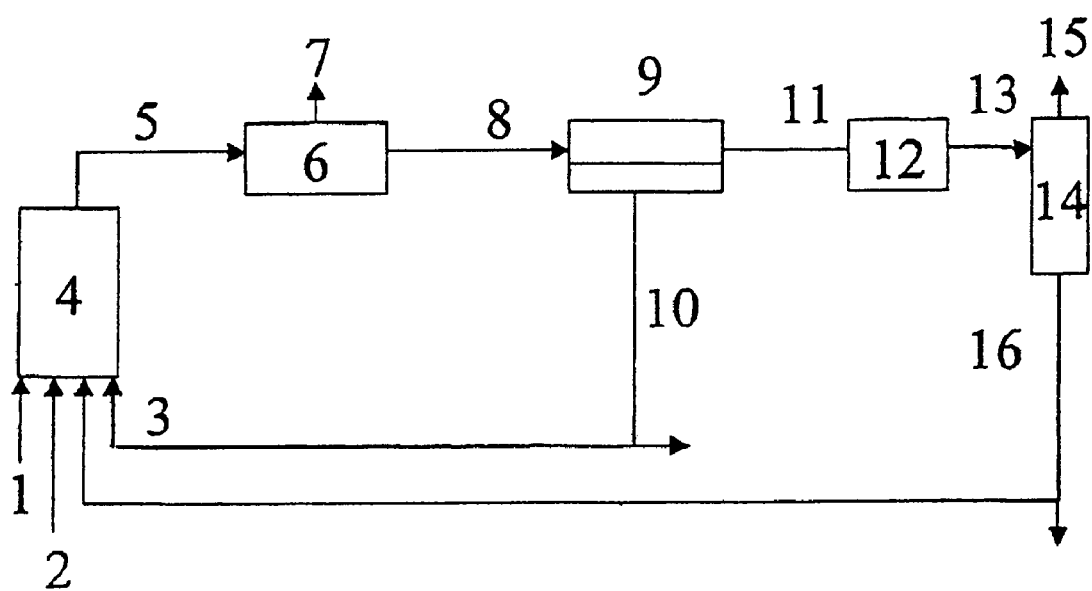
FIG. 1 shows a reaction scheme for the process of the present invention.

The present invention accordingly provides a process for the catalytic hydroformylation of olefinically unsaturated compounds having from 3 to 24 carbon atoms using an unmodified catalyst comprising at least one metal of groups 8 to 10 of the Periodic Table of the Elements, wherein the hydroformylation is carried out in the presence of at least one cyclic carbonic ester of the formula I

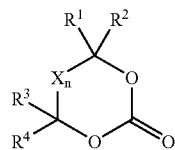

where

R¹, R², R³, R⁴ are identical or different and are each H or a substituted or unsubstituted aliphatic, alicyclic, aromatic, aliphatic-alicyclic, aliphatic-aromatic or alicyclic-aromatic hydrocarbon radical having from 1 to 27 carbon atoms, n is 0–5

X is a divalent substituted or unsubstituted, aliphatic, alicyclic, aromatic, aliphatic-alicyclic or aliphatic-aromatic hydrocarbon radical having from 1 to 27 carbon atoms, with the proportion of the carbonic ester being at least 1% by weight of the reaction mixture.

The use according to the invention of carbonic esters as solvents makes it possible to carry out the hydroformylation in the presence of unmodified catalysts, in particular a rhodium catalyst, and to reuse the unmodified catalyst.

The abovementioned modified ligands usually used in rhodium-catalyzed hydroformylation have a limited thermal stability which generally restricts the reaction temperature to 120–130° C. In the reaction of ethylenically unsaturated compounds which are difficult to hydroformylate, e.g. internal olefins and especially internal highly branched olefins, the ligand-modified rhodium catalysts display an industrially unsatisfactory activity at reaction temperatures limited by the thermal stability of the ligands and the customary reaction pressures of from 1 to 270 bar.

In contrast, unmodified rhodium has a significantly higher activity in the reaction of ethylenically unsaturated compounds which are difficult to hydroformylate. However, the low thermal stability is a disadvantage (N. S. Imyanitov, *Rhodium Express*, (1995), 10/11, 3–64). Examples of ethylenically unsaturated compounds which are difficult to hydroformylate are internal olefins and especially internal highly branched olefins which are present in the isomer mixtures obtained by dimerization and oligomerization of propene and n-butene, for example tripropene, tetrapropene, dibutene, tributene, tetrabutene and pentabutene.

The process of the invention has, in particular, the advantage that the catalyst has an increased long-term stability compared to catalysts used in conventional solvents. In addition, the solvent used makes the separation of the catalyst from the reaction mixture simple, since the catalyst is present in the phase in which the cyclic carbonic ester used as solvent is also present, regardless of the way in which the work-up is carried out (by distillation or via phase separation). This mixture can be returned directly as catalyst solution to the hydroformylation reactor. The separation of the output from the reactor into a fraction comprising product and unreacted starting material and a catalyst-containing fraction by phase separation is significantly more gentle on the catalyst than work-up by distillation. Thermal stress on the catalyst under reduced pressure does not occur, so that the formation of inactive metal catalyst species and metal-containing precipitates is avoided. Surprisingly, deactivation by formation of inactive metal catalyst species and metal-containing precipitates is also largely avoided in separation by distillation.

The process of the invention makes it possible to carry out the hydroformylation of internal highly branched olefins at temperatures of up to 220° C. using catalysts having a particularly high activity. The conversion and the selectivity of the hydroformylation, especially of internal highly branched olefins, can be increased in this way.

The process of the invention is described below by way of example without the invention being restricted to these particular examples. A person skilled in the art will be able to deduce further variants which are likewise subject matter of the present invention and whose scope is indicated by the description and the claims.

In the process of the invention for the catalytic hydroformylation of olefinically unsaturated compounds having from 3 to 24 carbon atoms, in particular olefins, using an unmodified catalyst comprising at least one metal of groups 8 to 10 of the Periodic Table of the Elements, the hydroformylation is carried out in the presence of at least one cyclic carbonic ester of the formula I

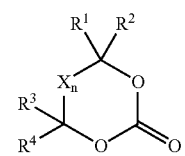

where

R¹, R², R³, R⁴ are identical or different and are each H or a substituted or unsubstituted aliphatic, alicyclic, aromatic, aliphatic-alicyclic, aliphatic-aromatic or alicyclic-aromatic hydrocarbon radical having from 1 to 27 carbon atoms, n is 0–5

X is a divalent substituted or unsubstituted, aliphatic, alicyclic, aromatic, aliphatic-alicyclic or aliphatic-aromatic hydrocarbon radical having from 1 to 27 carbon atoms, with the proportion of the carbonic ester being at least 1% by weight of the reaction mixture.

The substituents R¹ to R⁴ and X can be identical or different and be substituted by O, N, NH, N-alkyl or N-dialkyl radicals. Furthermore, these radicals can bear functional groups such as halogens (fluorine, chlorine, bromine, iodine), —OH, —OR, —C(O)alkyl, —CN or —C(O)Oalkyl. Furthermore, C, CH or CH$_2$ groups in these radicals can be replaced by O, N, NH, N-alkyl or N-dialkyl radicals if they are at least three carbon atoms away from the O atom of the ester group. The alkyl groups can once again have from 1 to 27 carbon atoms.

In the process of the invention, preference is given to using ethylene carbonate, propylene carbonate, butylene carbonate or a mixture thereof, for example a mixture (weight ratio=50:50) of ethylene carbonate and propylene carbonate, as cyclic carbonic ester.

In the process of the invention, the proportion of cyclic carbonic esters is from 1 to 98% by weight, preferably from 5 to 70% by weight but particularly preferably from 5 to 50% by weight, of the reaction mixture.

It is possible to use further solvents in addition to the cyclic carbonic esters. In particular process variants, the hydroformylation reaction of the invention is therefore carried out in the presence of at least one nonpolar solvent which is immiscible with the cyclic carbonic ester I. Carbonic esters of the formula I have a dielectric constant of over 30. The nonpolar solvents which are immiscible with the cyclic carbonic ester I and are used in the process of the invention have dielectric constants of less than 20, preferably from 1.1 to 10, particularly preferably from 1.1 to 5. The use of an additional, in particular nonpolar, solvent makes it possible, for example, to produce a reaction mixture and, in particular, output from the reactor which is present as a single phase or as two phases. It may in this way be possible to simplify a phase separation employed in the work-up of the output from the reactor. The reaction product of the hydroformylation can be extracted with a nonpolar solvent which is immiscible with the cyclic carbonic ester I, in which case the solvent can either be present in the reaction mixture during the reaction or be added only after the reaction is complete.

Possible nonpolar solvents are substituted or unsubstituted hydrocarbons having from 10 to 50 carbon atoms, e.g. the high-boiling by-products of the hydroformylation reaction, Texanol or the isomer mixtures obtained in the tetramerization or pentamerization of propene or butene with subsequent hydrogenation, i.e. tetrabutane, pentabutane, tetrapropane and/or pentapropane. It is likewise possible to use olefins having 3–24 carbon atoms, in particular the olefin used for the hydroformylation, as nonpolar solvent by carrying out the hydroformylation reaction to incomplete conversion (e.g. to a conversion of only 95%, preferably 90%, particularly preferably 80%) and/or adding further olefin to the reaction mixture during and/or after the hydroformylation reaction.

In the process of the invention, the proportion of nonpolar solvents is from 0 to 90% by weight, preferably from 5 to 50% by weight, particularly preferably from 5 to 30% by weight, of the reaction mixture.

To avoid by-products, the nonpolar solvents have to be largely inert under the reaction conditions of the hydroformylation reaction unless they are the olefinically unsaturated compound used.

In the process of the invention, the reaction mixture can be present as a single phase or as two phases in the hydroformylation reactor over the entire conversion range. However, it is also possible for the feed mixture to be initially made up of two phases at a low conversion and to become a single phase at higher conversions during the course of the reaction. It is possible for a single-phase feed mixture to become a two-phase product mixture during the process of the invention. In addition, the phase behavior can be strongly temperature-dependent. For example, a reaction mixture which is a single phase at the reaction temperature can separate into two phases on cooling. A reaction mixture which is present as two phases at the reaction temperature can likewise become homogeneous on cooling.

The process of the invention can be carried out using various catalytically active metals of groups 8 to 10 of the Periodic Table of the Elements, but is preferably carried out using rhodium. For the purposes of the present invention, unmodified catalysts comprising metals of groups 8 to 10 of the Periodic Table of the Elements are catalysts which comprise no modifying ligands. Modifying ligands are, for the purposes of the present patent application, compounds which contain one or more donor atoms of group 15 of the Periodic Table of the Elements. However, modifying ligands do not include carbonyl, hydrido, alkoxy, alkyl, aryl, allyl, acyl or alkene ligands, nor the counterions of the metal salts used for catalyst formation, e.g. halides such as fluoride, chloride, bromide or iodide, acetylacetonate, carboxylates such as acetate, 2-ethylhexanoate, hexanoate, octanoate or nonanoate. A particularly preferred unmodified catalyst is $HRh(CO)_3$.

The active catalyst complex for the hydroformylation reaction is formed from a salt or a compound of the metal (catalyst precursor) and synthesis gas. This advantageously occurs in situ during the hydroformylation. Customary catalyst precursors are Rh(I), Rh(II) and Rh(III) salts, for example acetates, octanoates, nonanoates, acetylacetonates or halides, and also rhodium carbonyls. The concentration of the metal in the reaction mixture is preferably in the range from 1 ppm to 1000 ppm, preferably in the range from 5 ppm to 300 ppm.

The starting materials for a hydroformylation by the process of the invention are compounds which contain ethylenically unsaturated C—C double bonds, in particular olefins or mixtures of olefins, especially monoolefins having from 3 to 24, preferably from 4 to 16, particularly preferably from 4 to 12, carbon atoms, having terminal or internal C—C double bonds, e.g. 1- or 2-pentene, 2-methyl-1-butene, 2-methyl-2-butene, 3-methyl-1-butene, 1-, 2- or 3-hexene, the $C_6$-olefin mixture obtained in the dimerization of propene (dipropene), heptenes, 2- or 3-methyl-1-hexene, octenes, 2-methylheptenes, 3-methylheptenes, 5-methyl2-heptene, 6-methyl-2-heptene, 2-ethyl-1-hexene, the isomeric $C_8$-olefin mixture obtained in the dimerization of n-butenes (dibutene), the $C_8$-olefin mixture obtained in the dimerization of isobutene (diisobutene), nonenes, 2- or 3-methyloctenes, the $C_9$-olefin mixture obtained in the trimerization of propene (tripropene), decenes, 2-ethyl-1-octene, dodecenes, the $C_{12}$-olefin mixture obtained in the tetramerization of propene or the trimerization of butenes (tetrapropene or tributene), tetradecenes, hexadecenes, the $C_{16}$-olefin mixture obtained in the tetramerization of butenes (tetrabutene) and olefin mixtures prepared by cooligomerization of olefins having different numbers of carbon atoms (preferably from 2 to 4), if appropriate after separation into fractions having an identical or similar chain length by distillation. It is likewise possible to use olefins or olefin mixtures which have been obtained by the Fischer-Tropsch synthesis and olefins which have been obtained by oligomerization of ethene or olefins which are obtainable via metathesis reactions. Preferred starting materials are $C_4$-, $C_6$-, $C_8$-, $C_9$-, $C_{12}$- or $C_{16}$-olefin mixtures. Furthermore, the process of the invention can be used for the hydroformylation of polymeric olefinically unsaturated compounds such as polyisobutene or 1,3-butadiene copolymers or isobutene copolymers. The molar mass of the polymeric olefins is of little consequence as long as the olefin is sufficiently soluble in the hydroformylation medium. The molar mass of the polymeric olefins is preferably below 10 000 g/mol, particularly preferably below 5 000 g/mol.

The volume ratio of carbon monoxide to hydrogen in the synthesis gas is generally in the range from 2:1 to 1:2, in particular 1:1. The synthesis gas is advantageously used in excess, for example in an amount up to three times the stoichiometric amount.

The hydroformylations are generally carried out at pressures of from 1 to 350 bar, preferably at pressures of from 15 to 270 bar. The pressure employed depends on the structure of the feed olefins, the catalyst used and the desired effect. Thus, for example, α-olefins can be converted into the corresponding aldehydes in high space-time yields in the presence of rhodium catalysts at pressures of less than 100 bar. In contrast, in the case of olefins having internal double bonds, in particular branched olefins, higher pressures are advantageous.

The reaction temperatures in the process of the invention are preferably from 20 to 220° C., more preferably from 100° C. to 200° C., particularly preferably from 150° C. to 190° C., in particular from 160 to 180° C. A reaction temperature of above 150° C. can, in particular, improve the ratio of terminal to internal double bonds, since at the higher temperatures more terminal double bonds are made available as a result of accelerated isomerization and increased hydroformylation in the preferred terminal position thus takes place.

The process of the invention can be carried out batchwise or continuously. However, continuous operation is preferred. Suitable reactors include virtually all gas-liquid reactors known to those skilled in the art, for example sparged stirred vessels or bubble columns or tube reactors with or without recirculation. Preference is given to cascaded bubble columns and tube reactors provided with static mixing elements.

The reactor output obtained in the process of the invention comprises possibly unreacted olefinically unsaturated compound (olefins), reaction products, reaction by-products, at least one cyclic carbonic ester, possibly a nonpolar solvent and the catalyst. Depending on the type and mass fraction of the olefinic compound(s) used as starting material, type and mass fraction of any nonpolar solvent present and type and mass fraction of the cyclic carbonic ester, the output from the reactor can be present as a single phase or as two phases. As mentioned above, phase separation can be achieved or prevented by appropriate additions of cyclic carbonic esters or a nonpolar solvent.

The work-up of the reactor output in the process of the invention can be carried out in two variants, depending on the phase behavior of the reactor output. In the case of a two-phase reactor output, preference is given to a work-up via phase separation as in Variant A, while in the case of a single-phase reactor output preference is given to using a work-up by distillation as in Variant B.

It can be advantageous for the major part of the synthesis gas to be removed by depressurization after the hydroformylation before the further work-up of the reactor output is carried out according to variant A or B.

Variant A

In this process variant, the two-phase reactor output from the hydroformylation reaction is preferably separated by phase separation into a fraction comprising predominantly the catalyst and the cyclic carbonic ester or esters and a fraction comprising predominantly the hydroformylation products and unreacted olefins or olefinically unsaturated compounds.

This process variant can be employed when an optional further nonpolar solvent is used. The nonpolar solvent can be identical to the starting olefin, so that either the hydroformylation reaction is not carried out to full conversion (e.g. only to 95%, preferably 90%, particularly preferably 80%) and/or further olefin is added to the reaction mixture during and/or after the hydroformylation reaction.

Variant A of the process of the invention is illustrated by FIG. 1 without the process being restricted to this embodiment: synthesis gas (1), olefins (2) and hydroformylation catalyst dissolved in a cyclic carbonic ester or a mixture of a plurality of cyclic carbonic esters (3) are reacted in the hydroformylation reactor (4). The reactor output (5) can optionally be freed of excess synthesis gas (7) in a depressurization vessel (6). The stream (8) obtained in this way is preferably separated in a separation apparatus (9) to give a heavy phase (10) which comprises the major part of the cyclic carbonic ester and the catalyst and also high-boiling by-products and a light phase (11) which comprises the hydroformylation products, unreacted olefin and, if applicable, the nonpolar solvent. The phase separation can be carried out at temperatures of from 0° C. to 130° C., preferably from 10° C. to 60° C. The phase separation can be carried out in, for example, a settler vessel. The phase separation in the separation apparatus (9) is preferably carried out under synthesis gas at a pressure of from 1 to 350 bar, more preferably from 15 to 270 bar, but particularly preferably at the same pressure as that employed in the hydroformylation reactor (4). The separation apparatus (9) can optionally be preceded by a heat exchanger for cooling the product stream (5) (not shown in FIG. 1). In an optional separation stage (12), catalyst residues can be removed from the stream (11). Stream (11) or (13) is then passed to the separation stage (14). Here, the reaction products (aldehydes and alcohols) and unreacted olefins (15) are separated off and passed to further work-up or hydrogenation. The olefin which has been separated off from the stream (15) can be returned to the same reactor or passed to an optional further reaction stage. The fraction (16) which has likewise been separated off comprises, for example, residual cyclic carbonic ester, the reaction products, any further nonpolar solvent added and high-boiling by-products. Fraction (16) can be discarded or recirculated to the hydroformylation reactor (4). A work-up in which undesirable by-products are discharged is advantageously carried out prior to recirculation. The catalyst separation in the separation apparatus (9) can be carried out as an extraction by at least part of the fraction (16) and/or at least part of the fresh olefin (2) being fed directly into the stream (8). The extraction is preferably carried out continuously and can be a single-stage extraction or be operated as a multistage process in countercurrent, cocurrent or cross-current. Catalyst-containing discharge streams, for instance from stream (10) or from the separation stage (12), can be worked up by known methods to recover the catalyst metal in reusable form.

Variant B

In this process variant, the homogeneous reactor output from the hydroformylation reaction is separated by distillation into a relatively low-boiling fraction comprising predominantly the hydroformylation products and possibly unreacted olefins or olefinically unsaturated compounds and a higher-boiling fraction comprising predominantly cyclic carbonic esters and catalyst.

Figure 2:
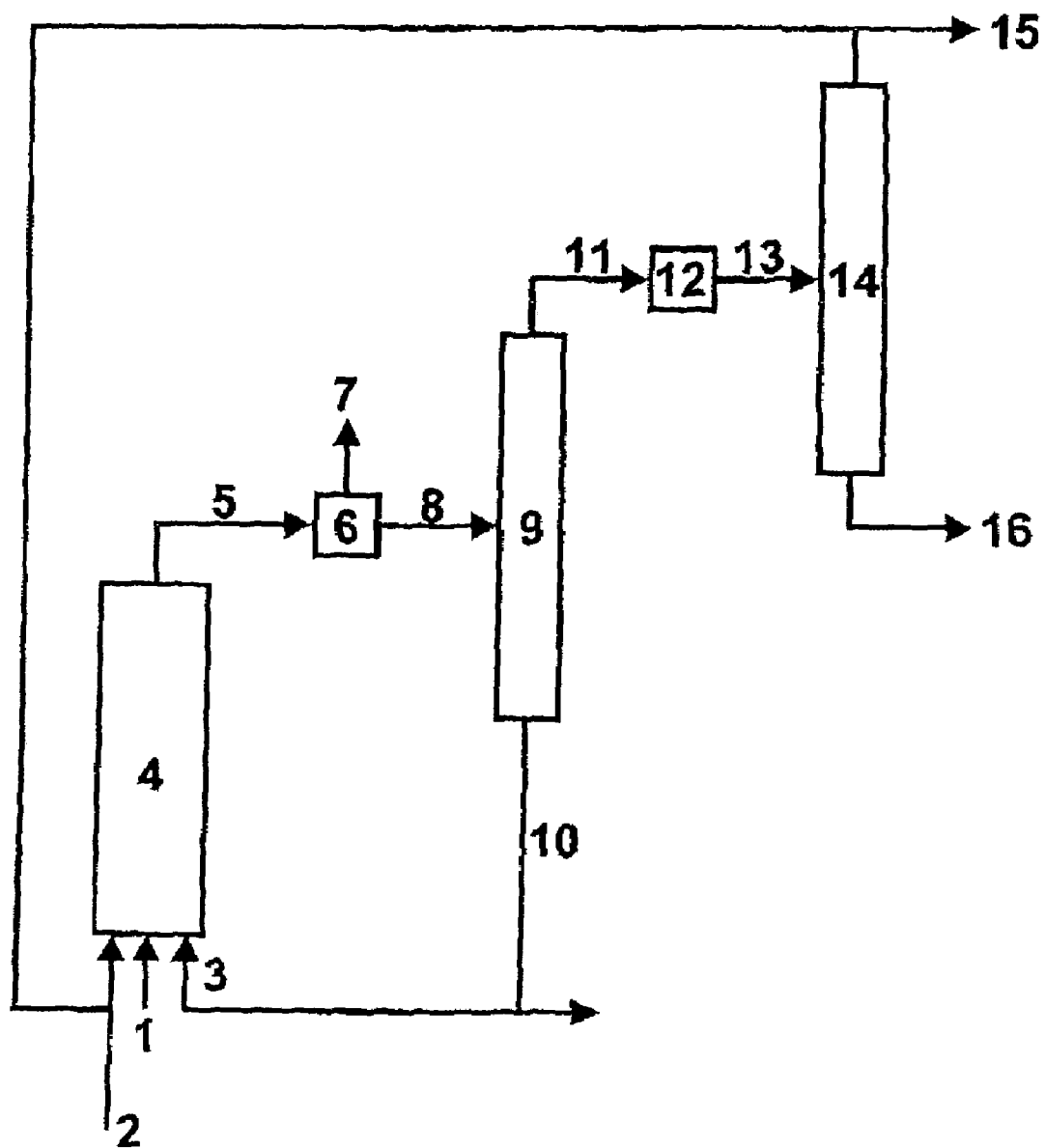
FIG. 2 shows a reaction scheme for the process of the present invention.

The variant B of the process of the invention is illustrated by FIG. 2 without the process being restricted to this embodiment: synthesis gas (1), olefins (2) and hydroformylation catalyst dissolved in a cyclic carbonic ester or a mixture of a plurality of cyclic carbonic esters (3) are reacted in the hydroformylation reactor (4). The reactor output (5) can optionally be freed of excess synthesis gas (7) in a depressurization vessel (6). The stream (8) obtained in this way is fed into a separation apparatus (9) and separated by distillation into a high-boiling fraction (10) which comprises the major part of the cyclic carbonic ester and the catalyst and a low-boiling phase (11) which comprises the hydroformylation products, unreacted olefin and, if applicable, nonpolar solvent. The catalyst-containing fraction (10) is recirculated to the hydroformylation reactor. This can optionally be preceded by a work-up step in which high-boiling by-products and/or catalyst degradation products are discharged (not shown in FIG. 2). Fraction (11) can optionally be freed of catalyst residues in a separation step (12). The stream 13 is then passed to the distillation stage (14). Here, the hydroformylation products (aldehydes and alcohols) (16) are separated from the unreacted olefin (15) by distillation. Catalyst-containing discharge streams, for instance from the stream (10) or from the separation stage (12), can be worked up to recover the catalyst metal in reusable form by methods known to those skilled in the art, e.g. from WO 02/20451 or U.S. Pat. No. 5,208,194. The hydroformylation products can subsequently be worked up further.

Unreacted olefin (15) can be returned to the same hydroformylation reactor or passed to an optional second reaction stage. When the process is carried out industrially, the separation apparatuses can be of various designs. The separation is preferably carried out by means of falling film evaporators, short-path evaporators or thin film evaporators or combinations of these apparatuses. The advantage of such a combination can be, for example, that still dissolved synthesis gas and the major part of the products and unreacted starting materials can be separated off from the catalyst-containing alkylene carbonate solution in a first step (for example in a falling film evaporator or flash evaporator) and the removal of the remaining alkylene carbonates and the separation of products and unreacted starting materials can then be carried out in a second step (for example in a combination of two columns).

The reactor outputs which have been freed of catalyst, excess synthesis gas and the major part of the solvent (i.e. the cyclic carbonic ester or a mixture of a plurality thereof) in either of the two variants A and B of the process of the invention are preferably separated further into aldehydes (alcohols), olefins, solvents and by-products. This can, as is known, be achieved by, for example, distillation. Olefin and/or solvent (alkylene carbonate and/or nonpolar solvent) which have been separated off from the output from the reaction or the hydroformylation products can be recirculated to the hydroformylation reaction.

The abovementioned variants of the process of the invention include the separation of the reactor output and optionally the hydroformylation products; this can be carried out, for example, by distillation. However, the use of other separation processes, e.g. extraction as described, inter alia, in WO 01/68247, EP 0 922 691, WO 99/38832, U.S. Pat. No. 5,648,554 and U.S. Pat. No. 5,138,101 or permeation as described, inter alia, in DE 1953641, GB 1312076, NL 8700881, DE 3842819, WO 9419104, DE 19632600 and EP 1103303, is also possible. When the separation is carried out industrially, various methods can be employed. The separation is preferably carried out by means of falling film evaporators, short-path evaporators or thin film evaporators or combinations of these apparatuses. The extractive separation is advantageously carried out continuously. It can be configured as a single-stage process or be operated as a multistage process in countercurrent or crosscurrent.

In all process variants, the fraction comprising the catalyst is advantageously recirculated to the hydroformylation reaction. This is of course independent of the composition of the fractions in which the catalyst is dissolved.

When the target products are not the aldehydes themselves but instead the alcohols derived from them, the reaction product mixture which has been freed of synthesis gas and catalyst and possibly of solvent can be hydrogenated before or after olefin has been separated off and subsequently be worked up by distillation to give pure alcohol.

The process of the invention can be carried out in one or more stages. Here, it is possible for the first hydroformylation reaction to be followed by a second hydroformylation stage which also converts the internal olefins, especially the internal highly branched olefins, which are difficult to hydroformylate into the desired aldehydes under more drastic reaction conditions (for example higher temperature and/or higher pressure). However, preference is given to unreacted olefins and hydroformylation products (aldehydes and alcohols) being carried out first and the unreacted olefins being recirculated to the same hydroformylation stage or passed to a second hydroformylation stage or even further hydroformylation stages. In such a case, the second hydroformylation stage can be carried out using a completely different catalyst system, i.e. a different catalyst metal or a ligand-modified catalyst metal. It can also be advantageous to add a higher concentration of catalyst to the unreacted olefins in this stage in order to convert olefins which are relatively difficult to hydroformylate into the desired products. In all cases, it is necessary to add the abovementioned amount of the cyclic carbonic esters in the further hydroformylation stages.

In the process of the invention, the olefinically unsaturated compounds used can also include compounds which are obtained as unreacted olefinically unsaturated compounds from the reactor output of a first hydroformylation reaction. Here, the entire reaction product mixture or only part thereof, in particular a part which comprises the predominant part of the unreacted olefinic compounds from the first stage, can be used. It can be advantageous in this process variant for the first hydroformylation reaction to be carried out in the presence of a ligand-modified catalyst.

EXAMPLES

The following examples are merely for the purposes of illustrating the invention and do not restrict its scope which is defined exclusively by the description and the claims.

Example 1

(Variant A)

560 g of propylene carbonate, 560 g of tri-n-butene and 0.0888 g or 0.0225 g of rhodium(II) nonanoate, corresponding to a rhodium concentration of 5 ppm or 20 ppm of rhodium based on the mass of the content of the reactor, were placed under a nitrogen atmosphere in a 2 l stirring autoclave. The autoclave was subsequently pressurized with synthesis gas (CO/H$_2$ 1:1 molar) and heated to the desired reaction temperature. The reactor pressure was monitored during heating. The reaction temperatures were from 130° C. to 180° C. The reaction pressure was 260 bar. During the reaction, further synthesis gas was introduced under pressure control. After 5 hours, the experiment was stopped and the reactor was cooled to ambient temperature. The reactor output was always made up of two phases and was free of rhodium precipitates.

The composition of the lighter hydrocarbon phase separated off in a phase separation vessel was determined by means of gas chromatography. The results of the gas chromatography and the reaction conditions such as temperature and rhodium concentration are summarized in Table 1.

TABLE 1

Hydroformylation of tri-n-butene at 260 bar and various temperatures for 5 hours. The proportions (in % by mass) reported relate to the composition of the lighter hydrocarbon phase, with any carboxylic ester and catalyst present having been subtracted. In Experiment 6, the catalyst solution obtained in the work-up of the reactor output from Experiment 5 was reused.

| No. | T/°C. | c (Rh)/ppm | C13-aldehydes/% | C13-alcohols/% | C12—HC/% | High boilers/% |
|---|---|---|---|---|---|---|
| 1 | 130 | 5 | 27 | 1 | 72 | 0 |
| 2 | 130 | 20 | 55 | 4 | 40 | 1 |
| 3 | 150 | 20 | 68 | 14 | 17 | 1 |
| 4 | 180 | 5 | 48 | 33 | 14 | 5 |
| 5 | 180 | 20 | 59 | 32 | 8 | 1 |
| 6 | 180 | 20 | 61 | 30 | 8 | 1 |

Example 2

(Variant B)

Di-n-butene (560 g) was hydroformylated in a manner analogous to Example 1. The reactor outputs from Experiments 7 to 13 were always made up of a single phase and were free of (rhodium) precipitates. In contrast to Example 1, the reactor output was analyzed by gas chromatography without work-up. The results of the gas chromatography and the reaction conditions such as temperature, pressure and rhodium concentration are summarized in Table 2.

TABLE 2

Hydroformylation of di-n-butene at various pressures, rhodium concentrations and temperatures. The proportions (in % by mass) reported relate to the composition of the reactor output, with carbonic ester and catalyst present having been subtracted.

| No. | T/°C. | p/bar | c (Rh)/ppm | C8—HC/% | C9-aldehydes/% | C9-alcohols/% |
|---|---|---|---|---|---|---|
| 7 | 150 | 50 | 40 | 67.5 | 30.4 | 2.1 |
| 8 | 150 | 250 | 40 | 3.1 | 87.6 | 3.3 |
| 9 | 170 | 150 | 5 | 26.3 | 66.6 | 27.1 |
| 10 | 170 | 250 | 5 | 4.5 | 78.1 | 17.4 |
| 11 | 170 | 250 | 40 | 4.0 | 20.5 | 75.5 |
| 12 | 180 | 50 | 40 | 66.8 | 17.5 | 15.7 |
| 13 | 180 | 150 | 40 | 9.9 | 23.3 | 66.8 |

Example 3

(Conventional Procedure)

Di-n-butene was hydroformylated as in Example 2 except that pentabutane was used as solvent in place of propylene carbonate. The reactor output from Experiment 14 displayed significant black (rhodium) precipitates. The aldehydes and unreacted olefins were subsequently separated off from the catalyst-containing solution in a thin film evaporator and the catalyst solution was used in another hydroformylation (Experiment 15). The results of the gas chromatography and the reaction conditions such as temperature, pressure and rhodium concentration are summarized in Table 2.

TABLE 3

Hydroformylation of di-n-butene at 150° C. and 250 bar in pentabutane. The proportions (in % by mass) reported relate to the composition of the reactor output, with pentabutane, by-products and catalyst present having been subtracted. In Experiment 15, the catalyst solution obtained in the work-up by distillation of Experiment 14 was reused.

| No. | T/°C. | p/bar | c (Rh)/ppm | C8—HC/% | C9-aldehydes/% | C9-alcohols/% |
|---|---|---|---|---|---|---|
| 14 | 150 | 250 | 40 | 75.4 | 23.4 | 1.2 |
| 15 | 150 | 250 | not known | 91.5 | 7.8 | 0.7 |

The absence of any rhodium precipitates in Experiments 1 to 13 indicates that the alkylene carbonate used as solvent has a particularly stabilizing effect on rhodium compounds. In contrast, when an alkane was used as solvent in the comparative experiment, a considerable quantity of rhodium precipitates and a drastic loss of activity when the catalyst was recirculated were observed (Experiments 14 and 15). In Experiment 6, the catalyst phase from Experiment 5 was used in a fresh hydroformylation. Within the limits of experimental accuracy, the olefin conversion remains constant.

The experiments demonstrate that the process of the invention offers a significantly higher chemo-selectivity to the desired aldehydes and, in addition, allows technically simple recirculation of the catalyst without significant deactivation.

The invention claimed is:

1. A process for the catalytic hydroformylation of an olefinically unsaturated compound having from 3 to 24 carbon atoms using an unmodified catalyst comprising rhodium, wherein the hydroformylation is carried out in the presence of a cyclic carbonic ester of the formula I

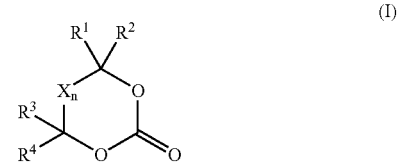

where $R^1$, $R^2$, $R^3$, $R^4$ are identical or different and are each H or a substituted or unsubstituted aliphatic, alicyclic, aromatic, aliphatic-alicyclic, aliphatic-aromatic or alicyclic-aromatic hydrocarbon radical having from 1 to 27 carbon atoms, n is 0–5

X is a divalent substituted or unsubstituted, aliphatic, alicyclic, aromatic, aliphatic-alicyclic or aliphatic-aromatic hydrocarbon radical having from 1 to 27 carbon atoms, with the proportion of the carbonic ester being at least 1% by weight of the reaction mixture.

2. The process as claimed in claim 1, wherein $R^1$, $R^2$, $R^3$, $R^4$ and X are substituted by identical or different substituents selected from the group consisting of O, N, NH, N-alkyl, N-dialkyl, fluorine, chlorine, bromine, iodine, —OH, —OR, —CN, —C(O)alkyl and —C(O)O-alkyl.

3. The process as claimed in claim 1, wherein said hydroformylation is carried out in the presence of from 5 to 50% by weight, based on the reaction mixture, of a solvent which is nonpolar compared to the cyclic carbonic ester I and is immiscible with the cyclic carbonic ester I.

4. The process as claimed in claim 1, wherein the reaction product from the hydroformylation is extracted with a nonpolar solvent which is immiscible with said cyclic carbonic ester.

5. The process as claimed in claim 3, wherein substituted or unsubstituted hydrocarbons having from 10 to 50 carbon atoms or olefins having from 3 to 24 carbon atoms are used as nonpolar solvent.

6. The process as claimed in claim 1, wherein said hydroformylation is carried out in the presence of HRh(CO)$_3$ as catalyst.

7. The process as claimed in claim 1, wherein the reaction product mixture from the hydroformylation reaction is separated into a fraction comprising predominantly the catalyst and the cyclic carbonic ester and a fraction comprising predominantly the hydroformylation products.

8. The process as claimed in claim 1, wherein a fraction comprising said catalyst is recirculated to the hydroformylation reaction.

9. The process as claimed in claim 1, wherein the cyclic carbonic ester is ethylene carbonate, propylene carbonate, butylene carbonate or a mixture thereof.

10. The process as claimed in claim 1, wherein the unreacted olefinically unsaturated compound is separated off from the reactor output or from the hydroformylation products and are returned to the same hydroformylation reaction or passed to a second hydroformylation reaction.

11. The process as claimed in claim 1, wherein the olefinically unsaturated compound is a compound which has been obtained as unreacted olefinically unsaturated compound from the reactor output of a first hydroformylation reaction.

12. The process as claimed in claim 11, wherein the olefinically unsaturated compound is a compound which has been obtained as unreacted olefinically unsaturated compound from the reactor output of a first hydroformylation reaction carried out in the presence of a ligand-modified catalyst.

13. The process as claimed in claim 4, wherein substituted or unsubstituted hydrocarbons having from 10 to 50 carbon atoms or olefins having from 3 to 24 carbon atoms are used as nonpolar solvent.

14. The process as claimed in claim 1, wherein said cyclic carbonic ester is present as a solvent in said reaction mixture.

15. The process as claimed in claim 1, wherein said cyclic carbonic ester is present in said reaction mixture in an amount of from 1 to 98% by weight.

16. The process as claimed in claim 1, wherein said cyclic carbonic ester is present in said reaction mixture in an amount of from 5 to 70% by weight.

17. The process as claimed in claim 1, wherein said cyclic carbonic ester is present in said reaction mixture in an amount of from 5 to 50% by weight.

18. The process as claimed in claim 1, wherein said cyclic carbonic ester is present in said reaction mixture in an amount of at least 5% by weight.

19. The process as claimed in claim 1, wherein said cyclic carbonic ester is present in said reaction mixture in an amount of from 5 to 98% by weight.

20. A process for the catalytic hydroformylation of an olefinically unsaturated compound having from 3 to 24 carbon atoms using an unmodified catalyst comprising at least one metal of groups 8 to 10 of the Periodic Table of the Elements, except cobalt, wherein the hydroformylation is carried out in the presence of a cyclic carbonic ester of the formula I

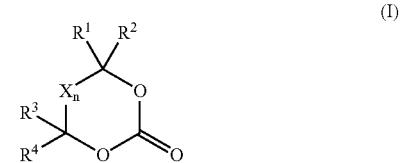

where $R^1$, $R^2$, $R^3$, $R^4$ are identical or different and are each H or a substituted or unsubstituted aliphatic, alicyclic, aromatic, aliphatic-alicyclic, aliphatic-aromatic or alicyclic-aromatic hydrocarbon radical having from 1 to 27 carbon atoms, n is 0–5

X is a divalent substituted or unsubstituted, aliphatic, alicyclic, aromatic, aliphatic-alicyclic or aliphatic-aromatic hydrocarbon radical having from 1 to 27 carbon atoms, with the proportion of the carbonic ester being at least 1% by weight of the reaction mixture.

21. The process as claimed in claim 1, wherein said cyclic carbonic ester is present in said reaction mixture in an amount of from about 50 to 98% by weight.

* * * * *

UNITED STATES PATENT AND TRADEMARK OFFICE
CERTIFICATE OF CORRECTION

| | | |
|---|---|---|
| PATENT NO. | : 7,193,116 B2 | Page 1 of 1 |
| APPLICATION NO. | : 10/519557 | |
| DATED | : March 20, 2007 | |
| INVENTOR(S) | : Moeller et al. | |

It is certified that error appears in the above-identified patent and that said Letters Patent is hereby corrected as shown below:

On the title page, Item (30), the Foreign Priority Data should read:
--[30]     Foreign Application Priority Data
    Aug. 31, 2002    (DE) ........................102 40 253
    Jun. 18, 2003    (DE) ........................103 27 435--

Signed and Sealed this

First Day of January, 2008

JON W. DUDAS
*Director of the United States Patent and Trademark Office*